United States Patent
Regittnig et al.

(10) Patent No.: US 8,303,533 B2
(45) Date of Patent: Nov. 6, 2012

(54) DEVICE AND METHOD FOR DELIVERY OF A PHYSIOLOGICALLY ACTIVE SUBSTANCE DEPENDING ON A MEASURED PHYSIOLOGICAL PARAMETER

(75) Inventors: Werner Regittnig, Graz (AT); Thomas Pieber, Graz (AT); Lukas Schaupp, Graz (AT); Martin Ellmerer, Graz (AT); Gerd Koehler, Graz (AT)

(73) Assignee: Medizinische Universitaet Graz, Graz (AT)

( * ) Notice: Subject to any disclaimer, the term of this patent is extended or adjusted under 35 U.S.C. 154(b) by 0 days.

(21) Appl. No.: 11/910,096

(22) PCT Filed: Mar. 29, 2006

(86) PCT No.: PCT/EP2006/002865
§ 371 (c)(1),
(2), (4) Date: Jul. 24, 2008

(87) PCT Pub. No.: WO2006/103061
PCT Pub. Date: Oct. 5, 2006

(65) Prior Publication Data
US 2009/0005724 A1    Jan. 1, 2009

Related U.S. Application Data

(60) Provisional application No. 60/734,944, filed on Nov. 9, 2005.

(30) Foreign Application Priority Data

Mar. 29, 2005  (AT) .................................. A 525/2005

(51) Int. Cl.
*A61M 31/00*    (2006.01)
(52) U.S. Cl. ............................................ 604/65; 604/31

(58) Field of Classification Search .................... 604/31, 604/65–67, 500–514; 600/366
See application file for complete search history.

(56) References Cited

U.S. PATENT DOCUMENTS 5,097,834 A * 3/1992 Skrabal ......................... 600/366
(Continued)

FOREIGN PATENT DOCUMENTS

AT    WO88/05643 A1    8/1988
(Continued)

*Primary Examiner* — Kevin C Sirmons
*Assistant Examiner* — Phillip Gray
(74) *Attorney, Agent, or Firm* — Robert A. Blaha; Smith Risley Tempel Santos LLC

(57) ABSTRACT

A device for delivery of glucose-regulating medication, particularly insulin, depending on the measured tissue glucose concentration, having a sensor for measuring the glucose concentration in tissue fluid, possibly a unit for removing fluid from subcutaneous tissue, as well as a container for the glucose-regulating medications, having a unit for subcutaneous delivery of the glucose-regulating medications, and having a unit connected to the glucose sensor for regulating the quantity of the glucose-regulating medication to be delivered depending on the measured tissue glucose concentrations. The device simulates the function of the natural pancreas and is constructed small and compact. The sensor for measuring the tissue glucose concentration or the unit for removing the tissue fluid is combined with the delivery unit for subcutaneous delivery of the glucose-regulating medication, particularly in a shared catheter, so that the measurement of the tissue glucose concentration is essentially performed at the location of the delivery of the glucose-regulating medication.

30 Claims, 10 Drawing Sheets

| U.S. PATENT DOCUMENTS | | | |
|---|---|---|---|
| 5,193,545 | A | 3/1993 | Marsoner et al. |
| 5,243,982 | A | 9/1993 | Moestl et al. |
| 6,017,318 | A | 1/2000 | Gauthier et al. |
| 6,458,118 | B1 | 10/2002 | Lent et al. |
| 6,558,351 | B1 | 5/2003 | Steil et al. |
| 6,770,030 | B1 | 8/2004 | Schaupp et al. |
| 2003/0083698 | A1 | 5/2003 | Whitehurst et al. |

| FOREIGN PATENT DOCUMENTS | | |
|---|---|---|
| DE | 19756872 | 7/1999 |
| EP | 0 367 752 A1 | 10/1990 |
| EP | 1166808 | 1/2002 |
| JP | 2004-283378 A1 | 10/2004 |

\* cited by examiner

DEVICE AND METHOD FOR DELIVERY OF A PHYSIOLOGICALLY ACTIVE SUBSTANCE DEPENDING ON A MEASURED PHYSIOLOGICAL PARAMETER

CROSS REFERENCE TO RELATED APPLICATION

The present application claims the benefit of the filing date of Austrian Patent Application 2B A 525/2005-1,2, filed Mar. 29, 2005, and of U.S. Provisional Patent Application 60/734,944, filed Nov. 9, 2005, the disclosure of which is hereby incorporated herein by reference.

TECHNICAL FIELD

The invention relates to a device for delivery of a physiologically active substance depending on a measured physiological parameter.

The invention also relates to a method for delivery of a physiologically active substance depending on a measured physiological parameter.

BACKGROUND

Diabetes mellitus is one of the most frequently occurring chronic illnesses worldwide. Diabetes mellitus is caused by a malfunction of the regulation of the carbohydrate metabolism. In this case, the insulin production by the β-cells in the pancreas is suppressed (type I diabetes) or abnormal (type II diabetes). Approximately 10-15% of diabetic patients are to be assigned to type I diabetes, which require externally supplied insulin for the breakdown of the blood glucose. The larger proportion of type II diabetic patients typically do not require externally supplied insulin. These patients may combat the metabolic illness with the aid of diet and orally supplied medications. The current treatment of type 1 diabetic patients comprises the administration of insulin doses through multiple subcutaneous insulin injections during the day. Measuring the blood sugar concentration is required to determine the dose before the administration of the insulin syringe. This is typically performed manually by the patient, usually by taking a blood drop at the fingertip and supplying it to a measuring device. The insulin dose is adapted to the current blood sugar value and administered subcutaneously in the form of a bolus injection.

An increasing number of type I diabetic patients also use insulin pumps, which deliver insulin continuously and thus simulate the natural function of the pancreas better. Insulin pumps of this type may also be implanted completely. With this type of therapy, extracorporeal glucose measurement is nonetheless necessary to be able to adapt the insulin dose accordingly.

Nonetheless, with the forms of insulin therapy used currently, one frequently exceeds or falls below the desired blood sugar level. A continuously elevated blood sugar concentration (hyperglycemia) results in the development of later diabetic complications, such as microangiopathy, neuropathy, and macroangiopathy. Falling below the normal blood sugar concentration (hypoglycemia) represents an extremely frequent acute complication in the treatment of insulin requiring diabetes. The consequences of hypoglycemia particularly relates to the central nervous system, since glucose is the main nutrient of the brain. The most important goal in insulin therapy is avoiding severe hypoglycemia but also reducing the late complications due to hyperglycemia. In order to be able to keep the blood sugar concentration continuously in a narrow target range, frequent measurements of the blood sugar are absolutely necessary in connection with the administration of appropriate insulin doses. The development of continuous glucose measurement methods is being worked on intensively to allow frequent or even continuous blood sugar measurement.

The goal is the development of an artificial endocrine pancreas which regulates the administration of insulin automatically on the basis of the measured blood sugar concentration. Because of stability problems with implanted glucose sensors, until now no artificial pancreases of this type have been able to be developed. However, the newest sensors for continuous measurement of the glucose concentration show improvements with regard to long-term stability, so that these types of support devices may be available for the treatment of type I diabetes in the foreseeable future.

A completely implantable artificial pancreas is described in U.S. Pat. No. 5,298,022 A, the blood sugar being ascertained via a microdialysis arrangement. The result of the blood sugar measurement is transmitted wirelessly to an insulin pump, which sets the insulin quantity to be delivered in accordance with the measured blood sugar value.

U.S. Pat. No. 6,558,351 B1 describes a device of the representational type, the sensor for measuring the tissue glucose concentration being positioned at a location of the body and the measured values being transmitted through telemetry to a unit for delivering the insulin, which is positioned at another location of the body. A problem in the measurement of the tissue glucose concentration is generally the conclusion of the blood glucose concentration, according to which the insulin quantity to be delivered is to be regulated. In addition, the arrangement of two catheters in the subcutaneous tissue for the measurement of the tissue glucose concentration and the delivery of the insulin is complex and stressful for the patients.

U.S. Pat. No. 6,770,030 B1 describes a catheter, using which measurement of the glucose concentration and delivery of insulin are possible simultaneously. However, there is a spatial separation between the insulin delivery unit and the glucose sensor in this type of catheter.

EP 1,166,808 A2 discloses an injection needle unit usable in a portable automatic syringe device, the injection needle unit comprising a feeding tube, an "L"-shaped injection needle member connected to one end of the feeding tube, a connector connected to the other end of the feeding tube, and a depressing member integrally formed with the injection needle member in such a fashion that the injection needle protrude perpendicularly from the depressing member, the depressing member being depressed against the skin of a user upon penetrating the injection needle member into the subcutaneous tissue of the user. The injection needle unit comprises a glucose sensor attached to the injection needle and adapted to penetrate the body of the user when the injection needle penetrates the body of the user. The glucose sensor comprises an electrode wire wound around an injection needle in the form of a core, an insulating layer coated over the injection needle to insulate the injection needle from the electrode wire, and an enzyme member fitted around a portion of the injection needle adjacent to the injection tip while being insulated from the electrode wire. The enzyme member and the electrode wire penetrating the body of the user when the injection needle penetrates the body of the user, and leads connected to the enzyme member and the electrode wire, respectively, to electrically connect the enzyme member and the electrode wire to a voltage sensing means included in the automatic syringe device.

U.S. Pat. No. 6,017,318 discloses a feedback controlled drug delivery system including the automated sampling and analysis of a patient sample and dosing the patient based on the analysis. Automated sampling may be performed by direct analysis of the patient sample, such as for the measurement of a blood sample coagulation state or a glucose level. The drug delivery system includes a sample set that has a bidirectional patient tube that allows for delivery of the patient sample to an analyzer, and at another time, the infusion of a therapeutic drug. A controller receives a measurement from the analyzer, and based on that measurement, adjusts the delivery of the therapeutic fluid. The sample set has a quick-clear Leur fitting that allows for more effectively clearing a first fluid from a Leur fitting when starting a second fluid. The system also has a reagent cassette holder that protects, using a foam gasket, a reagent on a sample slide. Further, the system provides an interlock apparatus that assures a sample tube is occluded by either or both a slide clamp and by a platen arm compressing the sample tube to a peristaltic pump.

JP 2004-283378 discloses a drug injector provided with a syringe storing insulin, a motor quantitatively guiding the insulin, an injection needle injecting the insulin guided from the syringe by the motor in the body of the patient, the sensor measuring the glucose concentration in the body of the patient and a microcomputer controlling an injection speed or an injection timing of the insulin to be guided by the motor based on the concentration measured by the sensor. This device is so constituted that the sensor and the injection needle are dipped in the glucose of the known quantity and concentration, the fixed quantity of the insulin is injected from the injection needle by the motor to dilute the glucose, and its concentration in the diluting process is measured by the sensor to adjust the sensor.

U.S. Pat. No. 5,097,834 discloses a process for determining parameters of interest in living organisms. For this purpose, a perfusion fluid is directly introduced in the tissues. After its partial balancing of the tissue parameter of interest, the perfusion fluid is collected and analyzed for the parameter of interest, as well as for endogenous or exogenous marker properties indicative of the degree of interaction between the perfusion fluid and the tissue in such a way that the parameter of interest can be determined with the help of such characteristic properties.

There may be a need for an efficient device and an efficient method for the delivery of a physiologically active substance in dependence of a measured physiological parameter.

SUMMARY

According to one exemplary embodiment of the invention, a device and a method for delivery of a physiologically active substance depending on a measured physiological parameter are provided.

According to one exemplary embodiment of the invention, a device for delivery of a physiologically active substance depending on a measured physiological parameter is provided, the device having a sensor for the measurement of the physiological parameter of a body, optionally a unit for removing liquid from the body, a container for the physiologically active substance, a unit for delivery of the physiologically active substance, and a unit connected to the sensor for controlling the quantity of the physiologically active substance to be delivered depending on the measured physiological parameter. The sensor for measuring the physiological parameter and/or the unit for removing the fluid from the body is or are combined with the unit for delivery of the physiologically active substance, so that the measurement of the physiological parameter is performed essentially at the location of the delivery of the physiologically active substance.

According to another exemplary embodiment of the invention, a method for delivery of a physiologically active substance depending on a measured physiological parameter is provided, the method comprising measuring the physiological parameter of a body, optionally removing fluid from the body, conveying the physiologically active substance from a container to a unit for delivery of the physiologically active substance, and controlling the quantity of the physiologically active substance delivered depending on the measured physiological parameter, the physiological parameter essentially being measured at the location of the body at which the physiologically active substance is delivered.

According to another exemplary embodiment of the invention, a device for delivery of a physiologically active substance depending on a measured physiological parameter is provided, the device comprising a container for (or filled with) a perfusion fluid containing the physiologically active substance, a unit for delivery of the perfusion fluid containing the physiologically active substance into the body, a sensor for measuring the physiological parameter of the body by an analysis of the perfusion fluid after an at least partial equilibration of the perfusion fluid with a body fluid, and a unit, which is connected to the sensor, for controlling the quantity of the physiologically active substance to be delivered depending on the measured physiological parameter, wherein the sensor for measuring the physiological parameter is combined with (or functionally coupled to) the unit for delivery of the perfusion fluid containing the physiologically active substance, so that the measurement of the physiological parameter occurs essentially at the location of the delivery of the physiologically active substance.

According to yet another exemplary embodiment of the invention, a method for the delivery of a physiologically active substance depending on a measured physiological parameter is provided, the method comprising delivering a perfusion fluid containing the physiologically active substance into a body, measuring the physiological parameter of the body by an analysis of the perfusion fluid after an at least partial equilibration of the perfusion fluid with a body fluid, and controlling the quantity of the physiologically active substance delivered depending on the measured physiological parameter, wherein the physiological parameter is measured essentially at the location at which the physiologically active substance is delivered.

The term "perfusion fluid" may particularly denote any carrier liquid in which the physiologically active substance is included, dissolved or diluted so as to obtain a solution of a physiologically active substance in a desired concentration. It is common practice to provide physiologically active substances, like insulin, in a liquid perfusate solution in which the physiologically active substances is contained. Such a "perfusate fluid" may have, for instance, chemical properties of the below-mentioned neutral solution or any other suitable carrier fluid. Particularly, the skilled person knows many examples for perfusion fluids which are appropriate for containing insulin or other physiologically active substances. A perfusion fluid may also be denoted, for example, as a neutral solution, a rinse fluid, or a cleaning fluid.

According to the previously mentioned exemplary embodiments, the spatial extension of the injected fluid at the position at which the physiologically active substance (for instance insulin) is inserted or introduced in the body and the position at which the value of the physiological parameter (for instance a glucose level) is measured, may be of interest.

The perfusate fluid introduced in the body of course has a non-zero volume or, in other words, a three-dimensional extension. At a border area between this fluid volume (formed by the injected perfusion fluid and the physiologically active substance dissolved therein) and the surrounding or adjacent body fluid (particularly tissue fluid or interstitial fluid), it is believed that an exchange of molecules may occur between these two liquid phases (for instance by mechanisms like diffusion, osmosis-like phenomena, convectional mixing, etc.). Particularly, it is believed that insulin as the physiologically active substance diffuses into the body fluid, and glucose diffuses from the tissue fluid into the "drop" of injected perfusion fluid. These phenomena are believed to occur due to a temporary non-equilibrium or concentration gradient between the area of influence of the delivered insulin (that is the phase of the perfusion fluid including the physiologically active substance) and the tissue fluid. The two phases are selectively left uninfluenced for a predetermined waiting time or contact time or interaction time. This time interval may depend on a specific application and may be estimated by carrying out routine experiments, by applying theoretical or empiric models, or may be known from experience. The time interval may be in the order of magnitude between seconds and hours, particularly in the order of magnitude of minutes. Depending on the duration of the time interval, a partial or an essentially complete equilibrium for the concentrations of the physiologically active substance (insulin) and the substance to be measured for estimating the physiological parameter (glucose) is obtained. In this (partial) equilibration state, the concentration of the glucose is measured in the modified perfusate liquid. This may be performed particularly by one of the two following procedures: According to a first procedure, the modified perfusate can be removed (partially or essentially completely) from the body and may then be measured with an externally positioned sensor. According to a second procedure, the glucose level in the modified perfusate can be measured by a sensor located adjacent to or functionally coupled with the modified perfusate in the body.

In the context of such an embodiment, a calibration may be performed for refining the estimation of an appropriate amount of physiologically active substance to be administered, for instance based on one or more endogenous markers (for instance by measuring the electrical conductivity of the perfusion fluid comprising components of the body fluid) and/or based on one or more exogenous markers (for instance mannitol supplied to the perfusion fluid). Such a calibration unit may also fulfil the function to estimate or detect information with regard to the degree of equilibration (and/or degree of mixture, degree of dilution, etc.) of the perfusion fluid with the body fluid. For details concerning as to how to realize a calibration unit as such, further reference is made, for instance, to U.S. Pat. No. 5,097,834 which is hereby—particularly with respect to the portions of this document dealing with calibration—incorporated by reference in its entirety in the disclosure of this application.

The device may therefore comprise a marker sensing unit adapted to sense at least one value of at least one marker parameter of the fluid sample. Particularly, such a marker parameter may be an endogenous marker parameter. In this regard, explicit reference is made to the disclosure with respect to calibration using endogenous markers of WO 88/05643.

The term "endogenous marker" may particularly denote a substance whose concentration is known and regulated in the body fluid sample, for instance in interstitial fluid. By determining (or knowing) a concentration of one or more such markers, possible disturbing influences on the fluid levels of the substances (that is to say concentration or dilution of different substances in the body fluid) can be estimated and then used for compensation. Thus, it may be possible to compensate for errors in the estimation procedure. Therefore, both can be achieved, a higher reliability of the measured parameter and a soft treatment of the body under investigation.

Additionally or alternatively, the marker sensing unit may be adapted to sense an exogenous marker parameter.

The term "exogenous marker" may particularly denote a substance which is introduced from external into a (for example human) body under investigation. Further, the term "exogenous marker" may particularly denote a substance which is not produced by the (for example human) body, but may be produced artificially or by another organism. Examples for such exogenous markers are dyes or sugar-like substances such as mannitol or inulin. Mannitol and inulin are not taken up by certain human cell types (e.g., muscle and adipose tissue cells) and thus their distribution space is restricted to the vascular and interstitial space of these tissues. Adding such a substance to the perfusion fluid and measuring its concentration in the perfusion fluid after exchange of the perfusion fluid with a body fluid may allow to estimate the degree of equilibration (and/or degree of mixture, degree of dilution, etc.) of the perfusion fluid with this body fluid.

Exemplary endogenous marker parameters are ion concentrations of the body fluid sample, for instance of interstitial fluid, and particularly $Na^+$ or $K^+$ ion concentrations.

Particularly in case of an ex vivo measurement of the physiological parameter (for instance the glucose level), the perfusate may be used as the physiologically active substance (for instance insulin) carrying source, and also as the physiological parameter (for instance the glucose level) providing probe.

Particularly in case of an ex vivo measurement of the physiological parameter (for instance the glucose level), the degree of equilibration (or degree of mixture) after the introduction of the physiologically active substance (for instance insulin) may be estimated using endogenous and/or exogenous markers, and the externally measured physiological parameter (for instance the glucose level) may be calibrated accordingly.

Particularly in case of an in vivo measurement of the physiological parameter (for instance the glucose level), a possible dilution when introducing the physiologically active substance (for instance insulin) containing perfusion fluid may be estimated by calibrating using endogenous and/or exogenous markers, and the amount of the physiologically active substance (for instance insulin) to be delivered subsequently may be adjusted accordingly.

The perfusion fluid to be injected in the (human) body may comprise a component of the physiologically active substance (for instance insulin). Moreover, the perfusion fluid to be injected in the (human) body may comprise or may be free of a substance indicative of the physiological parameter (for instance glucose). If the perfusion fluid to be injected in the (human) body does comprise the substance indicative of the physiological parameter (for instance the glucose), the concentration or amount of this substance may be pre-known or determinable. This concentration or amount may be (controlled to be) different from the concentration or amount in the body fluid (for example tissue fluid).

In the context of the calibration, the perfusion fluid to be injected in the (human) body may be free of the endogenous marker (for instance value of the electrical conductivity is essentially zero) or may comprise the endogenous marker in a (known or determinable) marker concentration different from the marker concentration in the body fluid (for example the tissue fluid). When using an exogenous marker, the perfusion fluid to be injected in the (human) body may comprise the exogenous marker in a known or determinable concentration.

For further improving the efficiency for delivering the physiologically active substance (for instance insulin), only a part of the perfusion fluid comprising the physiologically active substance (for instance insulin) introduced into the body may be used for the measurement of the physiological parameter (for instance glucose). This may be realized, for instance, by a pump system which generates an appropriate pressure difference between inlet and outlet of a catheter (i.e. between beginning an end of a perfusate column), so that a higher amount of the physiologically active substance (for instance insulin) containing perfusion fluid flows into the body/tissue (for example 5 μl/min) than the amount of the physiologically active substance (for instance insulin) being removed for measuring the value of the physiological parameter (for instance the glucose level). This may be realized using peristaltic pumps (see for instance FIG. 7).

According to one exemplary embodiment of the invention, a device is provided which allows a good simulation of the natural function of the pancreas over a long period of time. For high acceptance, the device may be constructed as small and compact as possible, so that it may be carried on or in the body easily. Disadvantages of constructions until now may be avoided or at least reduced.

According to an exemplary embodiment of the invention, a method is provided, by which the natural function of the pancreas is made possible over a sufficiently long period of time. In addition, a sufficiently good estimation of the blood glucose concentration from the tissue glucose concentration for optimum regulation of the delivery of the glucose-regulating medications may be provided by the method according to the invention.

In the following, embodiments of the device according to the invention are described. These embodiments also apply for the method according to the invention.

The device may comprise a unit for removing the perfusion fluid after the at least partial equilibration of the perfusion fluid with the body fluid. In such an embodiment, the position of removing the fluid essentially equals to the position at which the physiologically active substance is provided. However, in this case, the analysis of the physiological parameter may also be carried out outside of the body. Thus, an ex vivo application and/or an in vivo application is possible.

Still referring to the previously explained embodiment, additionally or alternatively to the sensor, the unit for removing the perfusion fluid after the at least partial equilibration of the perfusion fluid with the body fluid may be combined with the unit for delivery of the perfusion fluid containing the physiologically active substance, so that the measurement of the physiological parameter occurs essentially at the location of the delivery of the physiologically active substance. This spatial relationship may ensure to obtain meaningful results.

The sensor for measuring the physiological parameter and/or the unit for removing the perfusion fluid after the at least partial equilibration of the perfusion fluid with the body fluid may be combined with the unit for delivery of the perfusion fluid containing the physiologically active substance, so that the measurement of the physiological parameter occurs essentially in the perfusion fluid after at least partial equilibration with the tissue fluid. Thus, the perfusion fluid may serve simultaneously for transporting and providing the physiologically active substance on the one hand, and as a medium in which the physiological parameter is measured on the other hand.

The physiologically active substance may be a medication, particularly a glucose-regulating medication such as insulin, insulin analogues, glucagon, catecholamines, cortisol, or growth hormone. In this way, the supply of the physiologically active substance to the body may selectively and effectively influence the glucose level in the body or in specific parts of the body (e.g., tissue, blood). However, the physiologically active substance may also be any other arbitrary substance (such as aldosterone, bicarbonate, oxygen, phosphate) which has a functional influence on the body or organism. This particularly also includes any type of medicine, vitamin, carrier substances (such as artificial oxygen carriers), etc. The physiologically active substance may comprises at least one of the group consisting of insulin, glucagon, catecholamines, cortisol, growth hormone, aldosterone, phosphate, oxygen, oxygen carrier, and bicarbonate.

The physiological parameter to be measured may preferably be a glucose concentration in the body (particularly a tissue glucose concentration in the body), but may alternatively or additionally also be a lactate concentration in the body, an oxygen concentration in the body, an ion concentration (such as hydrogen-ion concentration, i.e., pH) in the body, a cholesterol concentration in the body, a quantity of bacteria in the body, a quantity of viruses in the body, or a medication concentration in the body. In this way, the measurement of such a physiological parameter or another physiological parameter may provide information about a current state of the body and thus be used as a meaningful decision criterion as to whether and to what extent a physiologically active substance is to be supplied to the body locally or globally. The physiological parameter comprises at least one of the group consisting of a glucose concentration in the body, a tissue glucose concentration in the body, a lactate concentration in the body, an oxygen concentration in the body, an ion concentration in the body, a cholesterol concentration in the body, a quantity of bacteria in the body, a quantity of viruses in the body, and a medication concentration in the body.

According to one exemplary embodiment, in a diabetes patient, a physiological parameter is measured, which may be the current glucose concentration and/or a current concentration of a glucose-regulating medication such as the insulin concentration. Based on the result of such a measurement, it may be decided whether and which physiologically active substance is to be supplied. For example, if too low a glucose concentration has been detected, glucose and/or glucagon may be supplied. In contrast, if too high a glucose concentration has been detected, insulin may be supplied. However, insulin is not the only glucose-regulating substance which may be supplied as physiologically active substance. Other substances may also be used for glucose regulation.

Another example of a physiological parameter and an assigned physiologically active substance is the lactate or oxygen concentration in the blood (as physiological parameter) and a bicarbonate, phosphate, or oxygen carrier infusion (as physiologically active substance). In the event of circulatory disorders in the tissue, the oxygen concentration in the blood or tissue may be reduced and the lactate concentration in the blood or tissue may be increased, because of a glucose metabolism whose efficiency is reduced. If such a scenario is measured using measurement of the lactate, pH and/or oxygen concentration in the blood or tissue, physiologically active substances such as bicarbonate, phosphate or artificial oxygen carrier may be introduced in order to (locally) increase oxygen delivery.

As an alternative to the scenario just described, an ion concentration (e.g., sodium or potassium concentration) in the body and/or in the fluid may be measured as a physiological parameter. Aldosterone (as physiologically active substance) regulates the electrolyte and water concentrations in the human body. It increases the resorption of sodium ions from the kidneys and thus increases the sodium level in the blood. Excretion of potassium ions and water ions may be stimulated. The potassium level in the blood may thus be reduced. Water is simultaneously retained. Aldosterone thus has an influence on the regulation of blood volume and blood pressure and may also be used as a physiologically active substance in the context of the invention.

The fluid which is removable from the body may be tissue liquid. Alternatively or additionally, the fluid may, however, also be blood, lymph, spinal fluid, urine, or other tissue. The term "fluid" may include any substance in this context which at least partially contains components in the liquid phase. Of course, solid and/or gaseous components may also be contained or dissolved in such a fluid and may even make up the predominant component of the fluid. Thus, the penetrated part of the body may be particularly subcutaneous tissue, an organ, a vein, an artery, and a blood vessel. Particularly when the calibration device is combined with the sensor for measuring the glucose level, an intravenous application of the device is possible. Also applications in the skin are possible, for instance by cutaneous microperfusion.

In particular, the delivery unit may be adapted for delivery of the physiologically active substance to subcutaneous tissue.

The unit for controlling the quantity of physiologically active substance to be delivered depending on the measured physiological parameter may be adapted to regulate the quantity of physiologically active substance to be delivered depending on the measured physiological parameter. While "controlling" in this context may particularly be understood to mean that an active control of the quantity to be delivered of the physiologically active substance may be performed by the value of the measured physiological parameter, a feedback functionality may clearly be provided if the unit is implemented as a regulatory unit. This may particularly be understood to mean that the concentration of the physiologically active substance may also be measured and (also) be used as a basis for the decision as to whether and in what quantity further physiologically active substance is supplied.

The unit for removing fluid from the body may be a microdialysis unit, a microperfusion unit, an ultrafiltration unit, a suction unit using one or more microneedles, or a transdermal extraction unit using reverse iontophoresis, ultrasound and/or osmotic pressure. While one of these implementations is preferred, any other removal possibility may also be employed.

The unit for removal of fluid from the body and the unit for delivery of the physiologically active substance may be formed by one (single) shared catheter for removal of fluid and/or measurement of the physiological parameter and/or delivery of the physiologically active substance. Spatial proximity between detection and active substance supply may thus be achieved.

Such a catheter may particularly be formed by a double-lumen catheter (i.e., a catheter having a first lumen and a second lumen), a perfusion fluid or a mixture of a perfusion fluid and the fluid removed from the body being able to be suctioned through the first lumen and the physiologically active substance being able to be delivered via the second lumen.

The sensor may be integrated in the unit for removal of fluid from the body and/or may be integrated in the unit for delivery of the physiologically active substance. A miniaturized arrangement may thus be provided, in which the detection and active substance supply are in a close functional relationship.

A unit for conveying the physiologically active substance from the container for the physiologically active substance to the unit for delivery of the physiologically active substance may be provided in the device. Furthermore, a unit for conveying a perfusion fluid and/or the fluid removed from the body from the unit for removing liquid from the body to the sensor may be provided in the device. Each of these two optional conveyor units, which may be provided separately from one another or jointly with one another, may be a pump, particularly a peristaltic pump.

The unit for conveying the physiologically active substance may simultaneously be usable for conveying the perfusion fluid and/or the fluid removed from the body from the unit for removal of fluid from the body to the sensor.

One or more containers for physiologically active substances, preferably of different concentrations and/or different active agents, may be provided in the device.

A container may be provided for a neutral solution. This may be understood to mean a buffer, water, or any arbitrary perfusion fluid, for example.

The at least one container for the physiologically active substance and the container for the neutral solution may be connected to a changeover switch, which may be connected to the unit for controlling the quantity of physiologically active substance to be delivered as a function of the measured physiological parameter, so that the quantity of physiologically active substance delivered may be adjusted by actuating the changeover switch.

The at least one container for the physiologically active substance and the container for the neutral solution may be connected to a mixer, which may be connected to the unit for controlling the quantity of physiologically active substance to be delivered depending on the measured physiological parameter, so that the quantity of the physiologically active substance delivered may be adjustable by actuating the mixer.

Furthermore, at least one container for collecting analyzed perfusion fluid and/or fluid removed from the body and conveyed through the device may be provided ("waste container").

The collecting container and the at least one container for the physiologically active substance and/or the container for the neutral solution may each be formed by a shared container having a movable wall (for example, automatic, controlled, or manual) for separating the physiologically active substance and/or the neutral solution from the collected perfusion fluid and/or fluid removed from the body.

The at least one container for the physiologically active substance and/or the (optional) container for neutral solution may be implemented as refillable. Therefore, the device may be operated in a resource-saving way.

A unit for calibrating the measurement of the physiological parameter may be provided in the device, through which the reliability and operational safety of the device may be improved.

The calibration unit may be formed by a unit for measuring the (electrical) conductivity of the perfusion fluid and/or the fluid removed from the body. For example, one or more measured conductivity values may be used for single or repeated calibration of the device.

The at least one container for the physiologically active substance, the container for the neutral solution, the collecting container for the analyzed fluid removed from the body, the unit for delivery of the physiologically active substance, the unit for controlling the quantity of the physiologically active substance to be delivered, and/or the calibration unit may be positioned in a shared housing. A device having small dimensions which is externally robust may thus be provided. The housing may be implemented as sealed and may be made of biocompatible materials or be enclosed by a biocompatible envelope.

Furthermore, a unit for the supply of electrical power may be positioned in the housing or outside the housing. The unit for the supply of electrical power may be formed by at least one, preferably rechargeable, accumulator. Alternatively, a disposable battery, a solar cell, or a fuel cell may also be used.

An electrical circuit (monolithically integrated or conventionally wired) may be provided for the inductive charging of the at least one accumulator.

According to an exemplary embodiment, a device for delivery of glucose-regulating medications depending on the measured tissue glucose concentration is provided, having a sensor for measuring the glucose concentration in the tissue fluid, possibly a unit for removing fluid from subcutaneous tissue, also having a container for the glucose-regulating medications, having a unit for subcutaneous delivery of the glucose-regulating medication, and having a unit connected to the glucose sensor for regulating the quantity of the glucose-regulating medication to be delivered depending on the measured tissue glucose concentration. The sensor for measuring the tissue glucose concentration or the unit for removal of the tissue fluid is combined with the delivery unit for subcutaneous delivery of the glucose-regulating medication, so that the measurement of the tissue glucose concentration is essentially performed at the location of the delivery of the glucose-regulating medication. It is particularly characteristic for the device that the glucose-regulating medication is also administered subcutaneously at the same location of the body at which the tissue glucose concentration is detected and/or the tissue fluid is removed for determining the tissue glucose concentration. This provides the advantage that only one unit is required both for measuring the tissue glucose concentration and also for the delivery of the glucose-regulating medication. This results in a reduced constructive outlay and thus a reduced installation size, but also results in a reduced stress of the patient, since only one catheter must be placed. Surprisingly, the relationship between blood glucose concentration and glucose concentration in the tissue fluid is stable even when the glucose-regulating medication is administered at the location of the glucose measurement in high doses. This has been shown on the basis of a study which is described below. The simultaneous analysis of tissue fluid to determine the glucose concentration and the delivery of glucose-regulating medications at the same location of the tissue with the aid of a single unit represents an exemplary aspect of the present invention.

The term glucose-regulating medications particularly includes insulin. However, the proteins amylin and extentadine, which have a glucose-reducing effect, like insulin, may also fall under this term. Glucagon, catecholamine, growth hormone, and cortisol may also be used as glucose-increasing hormones.

The removal unit and the delivery unit are advantageously formed by a shared catheter for removal of the tissue fluid or measurement of the tissue glucose concentration and subcutaneous delivery of the glucose-regulating medication. The catheter is inserted into the subcutaneous tissue at a suitable location of the body.

This catheter may operate according to the principle of microdialysis, in which an exchange of molecules between tissue fluid and a perfusion fluid occurs via a membrane.

The catheter may also operate according to microperfusion technology, mixing of the tissue fluid with a perfusion fluid occurring and the concentration of the appropriate substance, in the current case glucose, in this mixture being quantitated. The delivery of the glucose-regulating medication, particularly insulin, may also be performed according to the principle of microperfusion using a microperfusion catheter.

Alternatively to the above-mentioned methods, the catheter may also be formed by an ultrafiltration catheter, convection occurring because of pressure differences, through which fluid is drawn from the subcutaneous tissue, from which the glucose concentration may then be ascertained. The delivery of the glucose-regulating medications may also be performed according to the principle of ultrafiltration using an ultrafiltration catheter.

Finally, it is also possible to use a catheter according to the principles of iontophoresis and reverse iontophoresis. In this case, ions and uncharged species are removed from the tissue fluid by reverse iontophoresis and/or introduced into the tissue fluid in a targeted way using iontophoresis. Thus, according to these two principles, the glucose concentration may be measured in the tissue fluid and the glucose-regulating medication may also be introduced into the subcutaneous tissue.

According to a further exemplary embodiment of the present invention, the catheter is formed by a double-lumen catheter, the perfusion fluid and/or mixed perfusion and tissue fluid being suctioned through one lumen and the glucose-regulating medication being delivered in the direction of the subcutaneous tissue through the other lumen.

Alternatively to the above-mentioned constructions, the glucose sensor may also be integrated in the removal unit and/or delivery unit and the electrical signal corresponding to the measured glucose concentration may be transmitted via a line or wirelessly to the regulation unit of the device. This embodiment variation has the advantage that the glucose sensor may also be replaced simultaneously by exchanging the removal and delivery unit.

A unit for conveying the glucose-regulating medication from the container of the glucose-regulating medication to the delivery unit is advantageously provided.

Furthermore, a unit for conveying the perfusion and/or tissue fluid from the removal unit to the glucose sensor may also be provided. In the case of two conveyor units, a very high efficiency in the delivery of the glucose-regulating medication, particularly insulin, may be achieved by operating the conveyor unit for the glucose-regulating medication at a higher conveyance rate than the conveyor unit for the perfusion and/or tissue fluid.

The conveyor units may be formed by a pump, particularly a peristaltic pump.

The unit for conveying the glucose-regulating medication may also be used simultaneously for conveying the perfusion and/or tissue fluid from the removal unit to the glucose sensor. This again has a positive effect on the installation size of the unit, since only one unit has to be used both for suctioning the perfusion and/or tissue fluid and also for delivering the dose of the glucose-regulating medication.

Multiple containers for glucose-regulating medications, preferably having different concentrations, are advantageously provided. Depending on the measured glucose value, the glucose-regulating medication having a higher or lower concentration may be used and therefore may be used for a rapid and accordingly optimum reduction of the blood sugar in the shortest possible time. In this construction, the mixing of the glucose-regulating medication in different concentrations is performed externally.

Furthermore, a container for a neutral solution may be provided. The neutral solution is to be understood as a solution which does not contain the glucose-regulating medication, particularly insulin. This neutral solution is administered subcutaneously when the glucose concentration is in the target range and a reduction thereof is not necessary and/or when a reduction of the concentration of the glucose-regulating medication through mixing of the glucose-regulating medication with a neutral solution is desired. A continuous flow through the removal unit and/or delivery unit is achieved by the continuous delivery of glucose-regulating medications or the neutral solution.

In this case, the at least one container for the glucose-regulating medication and the container for the neutral solution may be connected to a changeover switch which is connected to the regulatory unit, the quantity of glucose-regulating medication delivered being adjustable by actuating the changeover switch. By changing the actuating times of the changeover switch, the quantity of glucose-regulating medication delivered over a specific period of time is thus defined.

It is also possible that the at least one container for the glucose-regulating medication and the container for the neutral solution are connected to a mixer, which is connected to the regulatory unit, so that the quantity of glucose-regulating medication delivered is adjustable by actuating the mixer. In this embodiment variation, the glucose-regulating medication is mixed with a neutral solution in accordance with the measured glucose concentration and administered subcutaneously to the patient in mixed form.

According to a further exemplary embodiment of the present invention, at least one container for collecting the analyzed perfusion fluid and/or tissue fluid is provided. By integrating a container of this type, it is also possible to implement the device as implantable, since all required components are contained. In addition, simpler replacement of the entire unit is achievable.

In this case, the waste container and the at least one container for the glucose-regulating medication and/or the container for the neutral solution may each be formed by a shared container having a movable wall for separating the glucose-regulating medication and/or the neutral solution from the collected perfusion and/or tissue fluid. This represents a compact construction variation which results in a reduced installation size of the entire unit and therefore in higher acceptance of the device.

The at least one container for the glucose-regulating medication and possibly the container for the neutral solution are preferably implemented as refillable. The refilling may, for example, be performed via a membrane with the aid of an injection. Alternatively, the container may also be implemented as replaceable, so that it may be exchanged easily by the patient or the manufacturer of the device.

A unit for calibrating the measurement of the tissue glucose concentration is advantageously provided. It is thus ensured that the measured values correlate well with the blood glucose concentration values and optimum regulation of the delivery of the glucose-regulating medication thus results.

This calibration unit may be formed easily by a unit for measuring the conductivity of the perfusate and/or tissue fluid.

The at least one container for the glucose-regulating medication, the possible container for the neutral solution, the possible container for the analyzed perfusate and/or tissue fluid, the delivery unit for delivery of the glucose-regulating medication, and the regulatory unit, and possibly the calibration unit, are advantageously positioned in a shared housing. A compact embodiment of the device is thus achievable.

If the housing is implemented as appropriately sealed and is made of biocompatible material or is enclosed by a biocompatible envelope, implanting of the device may be achieved.

A unit for the supply of electrical power is also advantageously positioned in the housing. An independently functioning device thus results.

The power supply unit may be formed by rechargeable accumulators.

It is advantageous in this case if a circuit for inductive charging of the accumulators is provided, so that it is possible to charge the accumulators via induction even when the device is implanted.

In the following, embodiments of the method according to the invention are described. These embodiments also apply for the device according to the invention.

According to one exemplary embodiment, a method for delivery of glucose-regulating medications as a function of the measured tissue glucose concentration is provided, the glucose concentration in the tissue fluid being measured, fluid possibly being removed from subcutaneous tissue, and the glucose-regulating medications being conveyed from a container to a unit for the subcutaneous delivery of the glucose-regulating medication, the quantity of the glucose-regulating medication delivered being regulated as a function of the measured tissue glucose concentration, and the glucose being measured essentially at the location of the subcutaneous tissue in which the glucose-regulating medication is delivered subcutaneously. The advantages of the method result from the above description of the device.

According to one exemplary embodiment of the invention, tissue fluid is taken from subcutaneous tissue and supplied to the sensor for measuring the tissue glucose concentration.

The tissue fluid may be removed according to the principle of microdialysis, of microperfusion, of ultrafiltration, of fluid suction using one or more microneedles, or of transdermal extraction using reverse iontophoresis, ultrasound and/or osmotic pressure and the glucose concentration may be determined therefrom.

The mixing of the glucose-regulating medication with a neutral solution, preferably an isomolar solution, may be performed in the device before the subcutaneous delivery.

Alternatively to this, the glucose-regulating medication may also be first mixed with the neutral solution directly in the subcutaneous tissue, by delivering both the glucose-regulating medication and also the neutral solution into the subcutaneous tissue.

Finally, the glucose-regulating medication may also be mixed externally with a neutral solution in predefined ratios and provided for subcutaneous delivery in the unit in the predefined mixing ratios.

The measurement of the tissue glucose concentration is preferably calibrated permanently in order to be able to make a reliable statement about the actual blood glucose concentration.

BRIEF DESCRIPTION OF THE FIGURES

Exemplary embodiments of the present invention are described in greater detail on the basis of the attached drawing. In the drawing.

DETAILED DESCRIPTION

Insulin is primarily used as glucose-regulating medication in the description of the figures. However, other substances may also be used.

Figure 1:
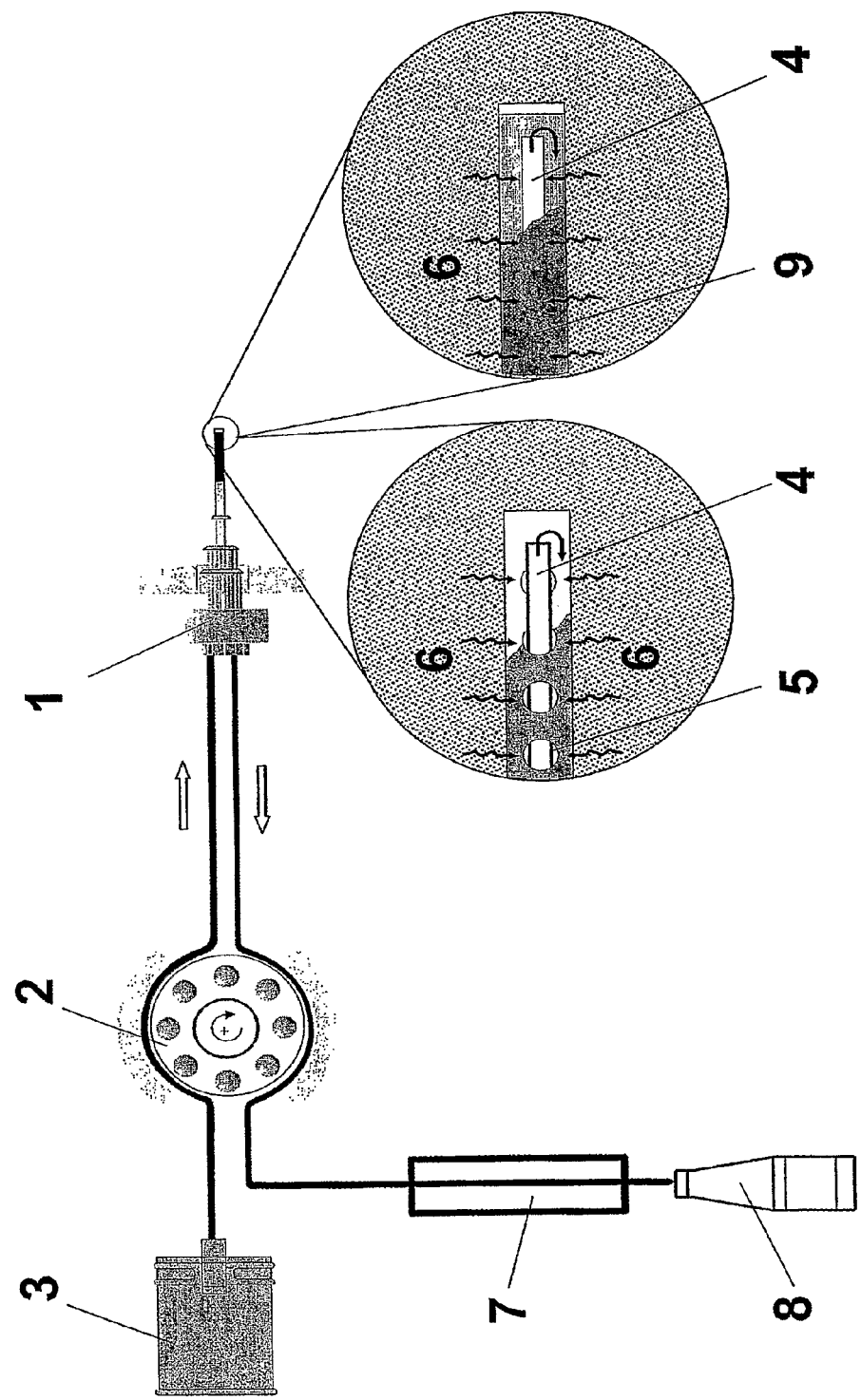
FIG. 1 shows a schematic block diagram of an ex-vivo glucose measurement unit.

FIG. 1 shows a schematic block diagram of an ex-vivo glucose measurement unit, in which a unit 1 for removing fluid from subcutaneous tissue, particularly a microperfusion or microdialysis catheter, is connected to a pump 2, preferably a peristaltic pump. Perfusion fluid 4 is introduced into the removal unit 1 with the aid of the pump 2 from a container 3. If the unit 1 is implemented for removing fluid from the subcutaneous tissue according to open microperfusion technology, as shown in the left part of the detail view of the tip of the removal unit 1, there is mixing of the perfusion fluid with the tissue fluid. The perfusion fluid 4 comes to the tip of the catheter through the interior of the double-lumen catheter and flows back via the external lumen, where the perfusion fluid 4 is mixed with the tissue fluid 6, which enters the cannula through corresponding perforations 5. The mixture of the perfusion fluid 4 with the tissue fluid 6 is transported by the pump 2 in the direction of glucose sensor 7, where the glucose concentration is measured. The mixture of the perfusion fluid 4 with the tissue fluid 6 is then collected in a container 8. Instead of the microperfusion catheter, a microdialysis catheter may also be used, as illustrated in the right detail view of the tip of the removal unit 1. In this case, a microdialysis membrane 9 is positioned on the catheter tip, via which molecular exchange occurs between tissue fluid 6 and perfusion fluid 4 and the glucose concentration in the tissue fluid may thus be measured.

Figure 2:
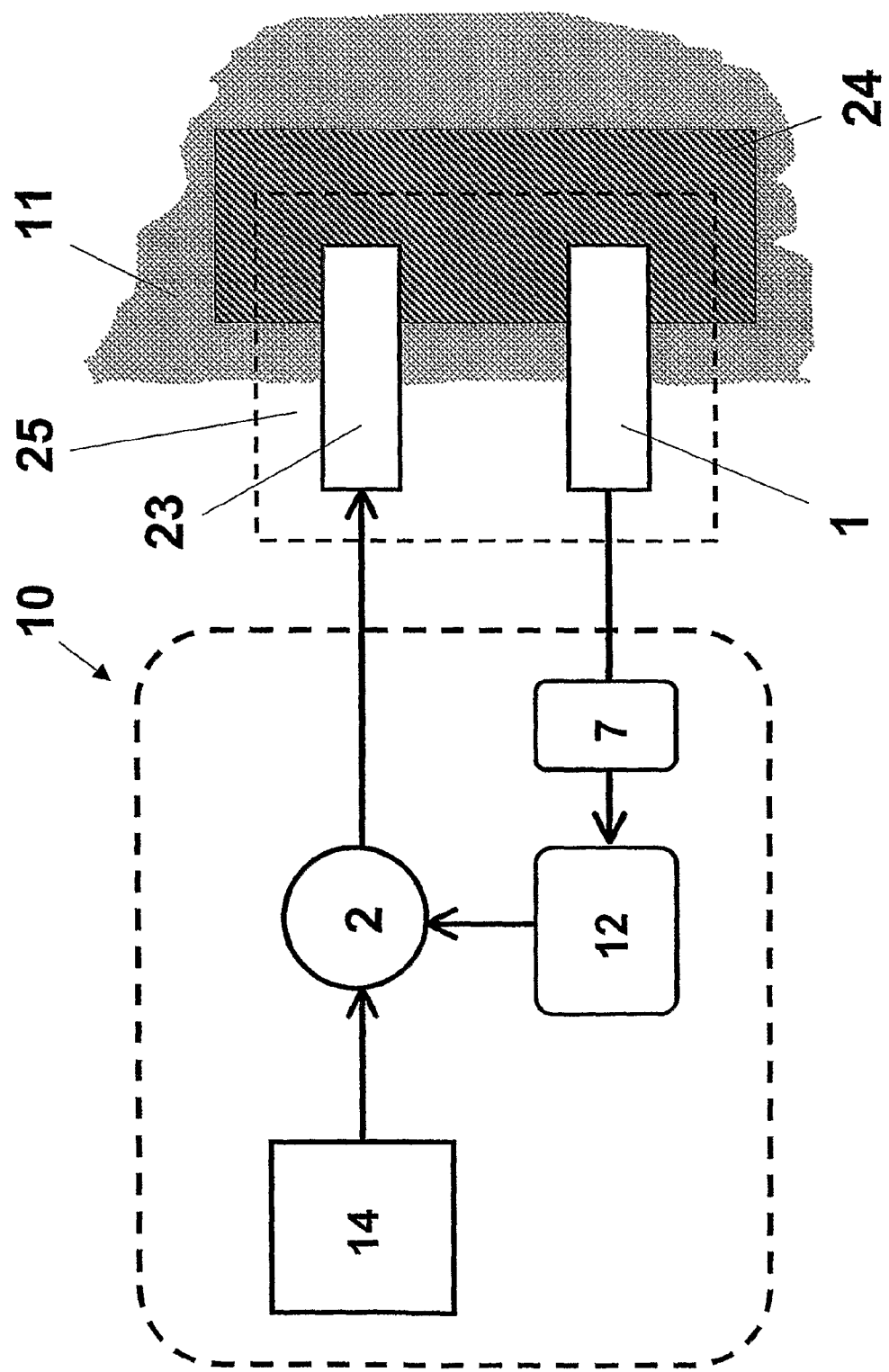
FIG. 2 shows a schematic block diagram of the device according to the invention.

FIG. 2 shows a schematic block diagram of the device 10 according to the invention for delivery of insulin and/or another glucose-regulating medication depending on the measured tissue glucose concentration having a sensor 7 for measuring the glucose concentration in the tissue fluid of a unit 1 for removing fluid from the subcutaneous tissue 11, as well as a container or reservoir 14 filled with a perfusion fluid (like a neutral solution) containing additionally a predetermined concentration of insulin and a unit 23 for the subcutaneous delivery of the insulin. A regulatory unit 12 receives the values measured by the glucose sensor 7 and regulates the insulin quantity to be delivered accordingly. The delivery of the insulin from the container 14 may be performed by a conveyor unit 2, particularly a pump. The glucose sensor 7 may also be integrated directly into the removal unit 1, upon which the measured values may be transmitted by wire or wirelessly from the glucose sensor 7 to the regulatory unit 12.

According to the invention, the sensor 7 for measuring the tissue glucose concentration or the unit 1 for removing the tissue fluid is combined with the delivery unit 23 for subcutaneous delivery of the insulin, so that the measurement of the tissue glucose concentration occurs essentially at the location of the insulin delivery. Therefore, the location of the measurement of the tissue glucose concentration and/or the removal of the tissue fluid for determining the tissue glucose concentration is in the area of influence 24 of the delivered insulin. This area of influence 24 is determined by the volume of perfusate introduced into the tissue and the diffusion capability of the insulin in the tissue fluid, the latter of which is, for example, 2 to 3 capillary lengths, i.e., 2 to 3 mm, around the unit 23 for delivering insulin. By measuring the glucose in this area of influence 24, stable ratios between tissue glucose concentration and plasma glucose concentration are provided and therefore an optimum regulation of the insulin delivery is achieved.

As indicated by reference numeral 24, the perfusate fluid introduced in the subcutaneous tissue 11 has a certain volume. At a border area between this fluid volume 24 and the surrounding tissue 11 fluid, due to concentration differences, it is believed that insulin diffuses into the tissue 11 fluid, and glucose diffuses from the tissue 11 fluid into the area of influence 24. For allowing for a selective at least partial equilibration, the two phases are left uninfluenced for a predetermined waiting time of, for instance, one minute. An equilibrium between the insulin and the glucose is thus obtained. Then, the concentration of the glucose is measured by the sensor 7 in the modified perfusate liquid 24.

The removal unit 1 and the delivery unit 23 are preferably formed by a shared catheter 25 for removing the tissue fluid or measuring the tissue glucose concentration and subcutaneously delivering the insulin. This catheter 25 may operate according to different principles, such as microdialysis, microperfusion, ultrafiltration, or iontophoresis/reverse iontophoresis.

Figure 3:
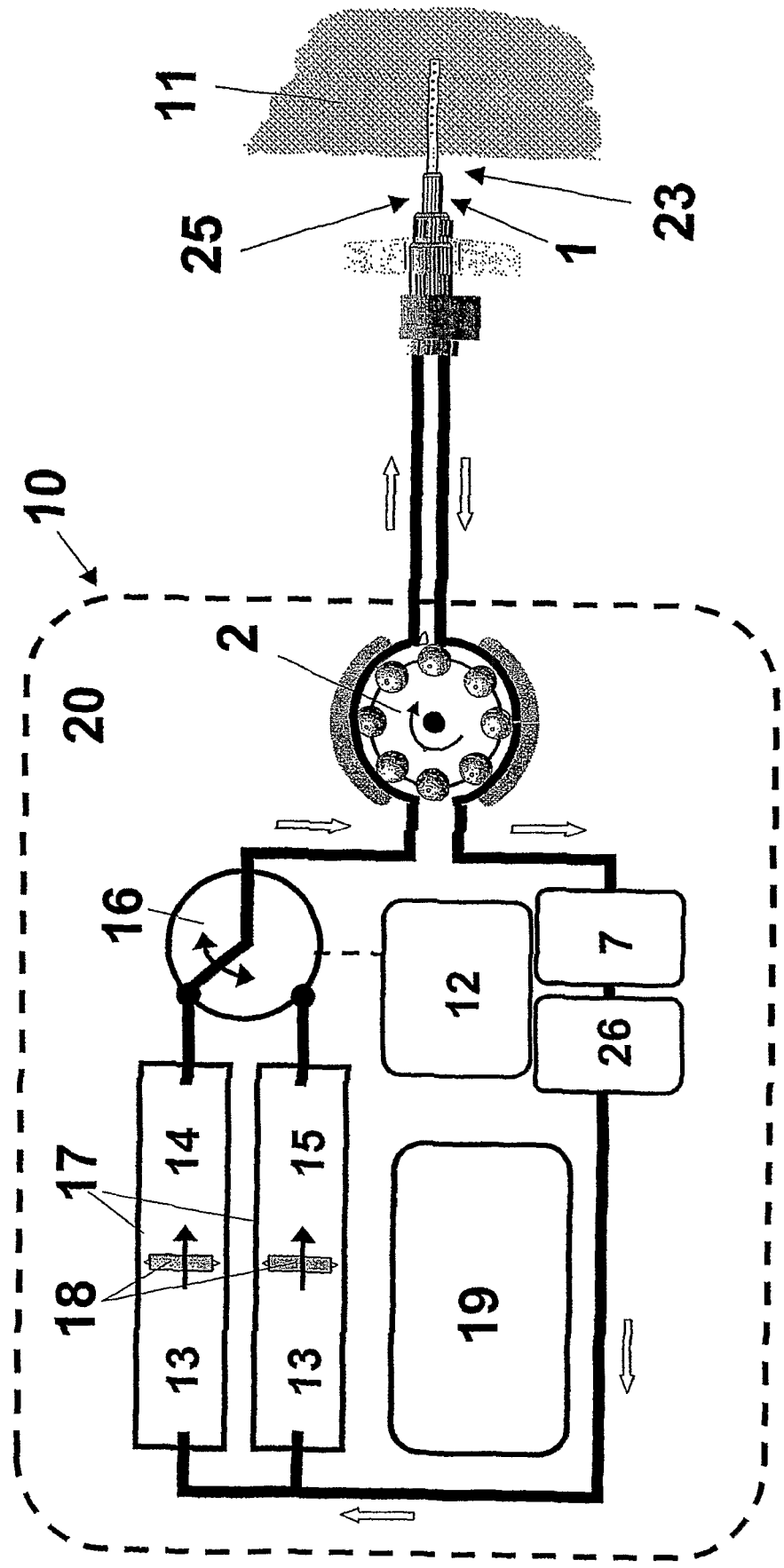
FIGS. 3 through 8 show different embodiment variations of the device according to the invention.

FIG. 3 shows a first embodiment of the device 10 according to the invention for delivery of insulin depending on the measured glucose concentration having a unit 1 for removing fluid from subcutaneous tissue 11 and a unit 23 for delivery of the insulin, which are formed by a shared catheter 25. The catheter 25 may, for example, be formed by a microdialysis or microperfusion catheter. The catheter 25 is penetrated into the subcutaneous tissue 11. The perfusion fluid or the mixture of perfusion fluid and tissue fluid is transported by a conveyor unit 2 to glucose sensor 7, where the glucose concentration is measured and passed to a regulatory unit 12. After the analysis of the glucose concentration, the perfusion fluid or the mixture of perfusion fluid and tissue fluid is collected in containers 13. Furthermore, the device 10 comprises at least one container 14 for insulin. Finally, a container 15 for a neutral solution, i.e., a solution which does not contain any glucose-regulating medication, particularly insulin, is provided. The regulatory unit 12 actuates a changeover switch 16, which is connected to the insulin container 14 or to the container 15 for the neutral solution depending on the measured glucose concentration. The changeover switch 16 is connected to the same conveyor unit 2 which is responsible for the transport of the perfusion fluid and/or tissue fluid, so that the insulin and/or the neutral solution may be conveyed in the direction of catheter 25 and delivered there to the subcutaneous tissue 11. Therefore, the delivery of the insulin in the desired quantities is caused by regulation of the changeover switch 16, and the mixture of the insulin with the neutral solution occurs in the subcutaneous tissue 11. The conveyance rate of the insulin is determined by changing the length of the time interval over which the insulin container 14 is connected to the conveyor unit 2. The longer the time slot, the higher the insulin quantity delivered. In the exemplary embodiment shown, the collecting containers 13 and the insulin container 14 are formed by a shared container 17, a movable wall 18 being provided for separating the insulin and the collected perfusion and/or tissue fluid. The container 15 for the neutral solution and the container 13 for the perfusion and/or tissue fluid may also be formed by a shared container 17 having a movable wall 18. A compact construction may thus be implemented. A unit 26 for calibrating the measurement of the tissue glucose concentration is advantageously also provided, which, for example, may be formed by a unit for measuring the conductivity of the perfusion and/or tissue fluid. Furthermore, a unit 19 for supplying electrical power is provided, which is preferably formed by rechargeable accumulators. The accumulators may be charged inductively. All components, with the exception of the removal unit 1, are advantageously housed in a shared housing 20. In order to allow implantation of the housing 20, it may be implemented as sealed and may be made of biocompatible material, such as titanium, or may be enclosed by a biocompatible envelope.

Figure 4:
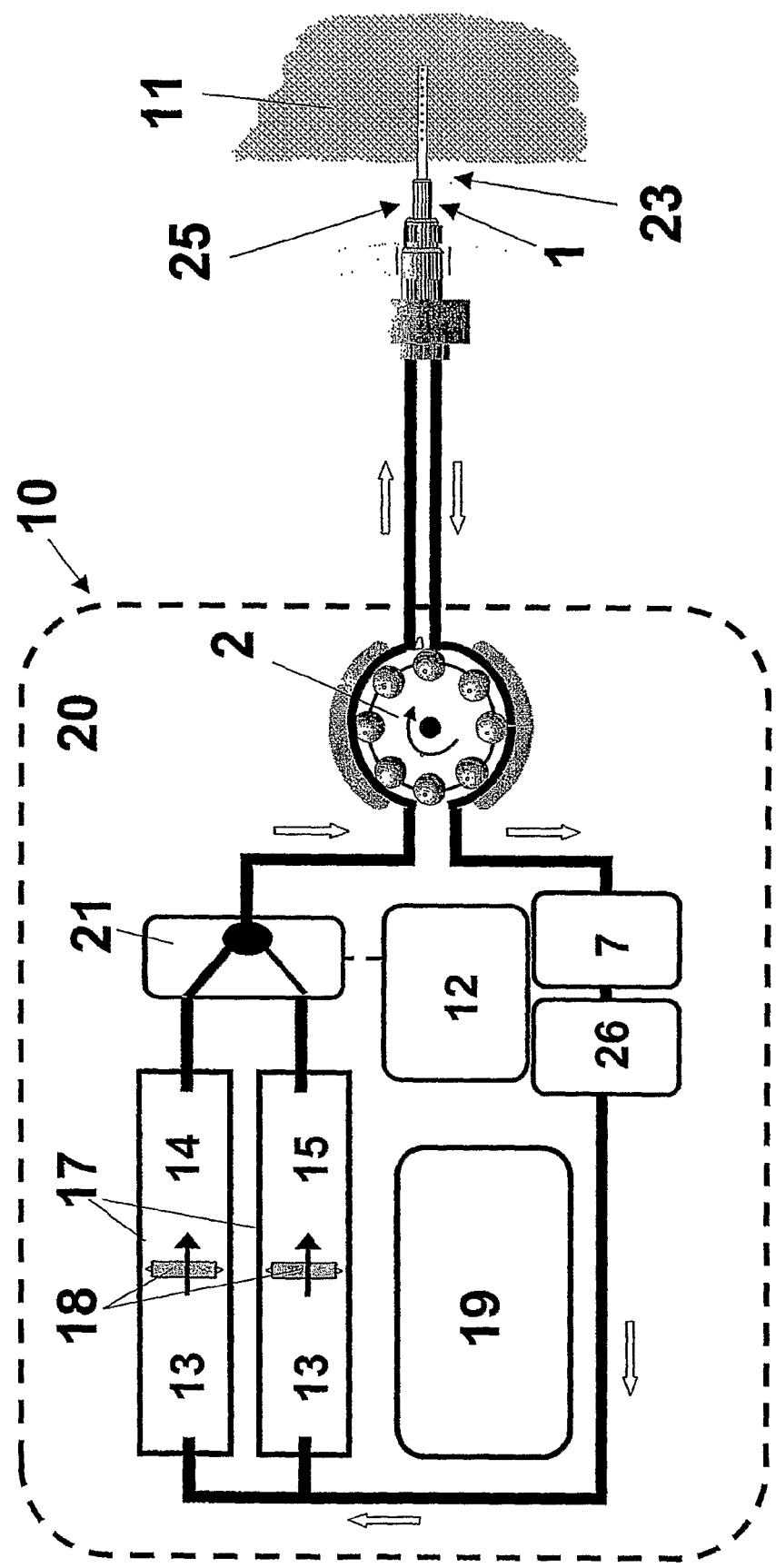

FIG. 4 shows a variation of the device 10 according to the invention, in which, instead of the changeover switch 16 shown in FIG. 3, a mixer 21 is provided, in which the insulin from the container 14 is mixed with the neutral solution from the container 15 depending on the measured glucose concentration and supplied to the catheter 25 for subcutaneous delivery.

Figure 5:
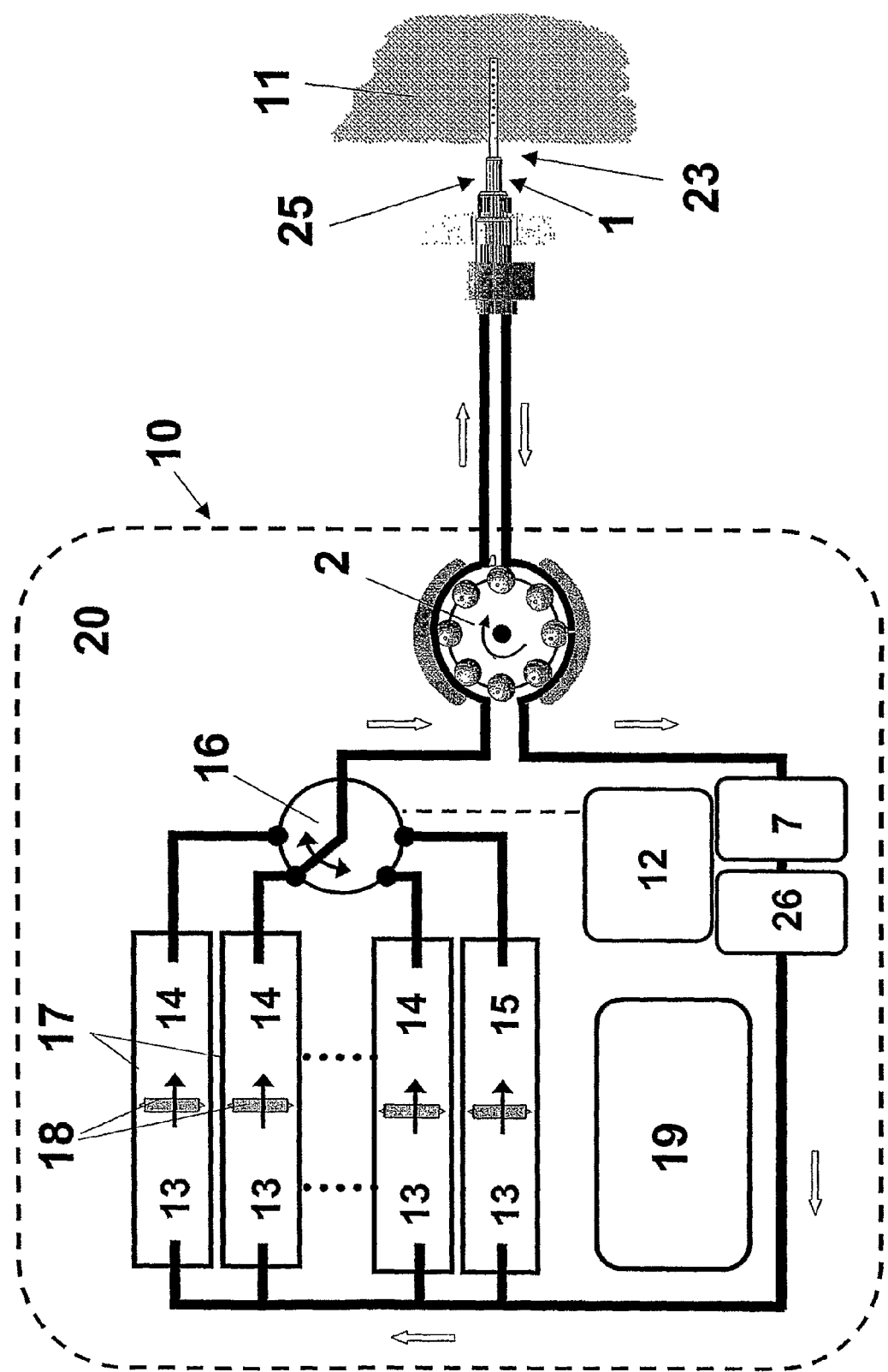

FIG. 5 shows a further embodiment of the device 10 according to the invention, in which multiple containers 14 for insulin, preferably of different concentrations, are provided. The changeover switch 16 has multiple settings in this embodiment, corresponding to the number of the insulin containers 14 and the container 15 for neutral solution. The changeover switch 16 is again changed over by the regulatory unit 12, so that depending on the measured glucose concentration, the insulin may be supplied at the suitable concentration to the catheter 25 and thus optimum setting of the glucose may be achieved.

Figure 6:
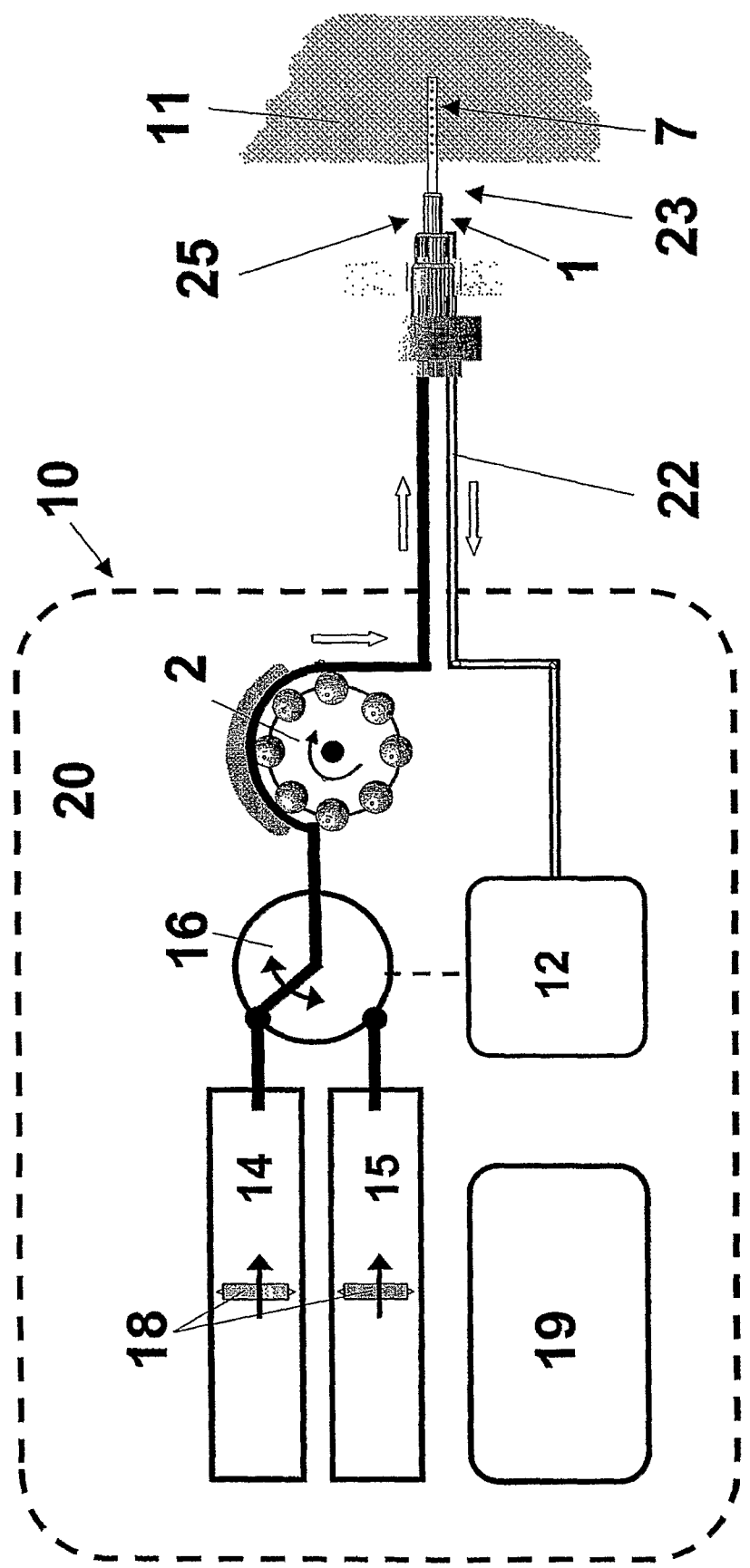

FIG. 6 shows a further embodiment of the device 10 according to the invention, in which the glucose sensor 7 is integrated in the catheter 25. The electrical signals which correspond to the measured glucose values are transmitted via a line 22 to the regulatory unit 12. In this case, the transmission of the signals may be performed electrically or optically.

Figure 7:
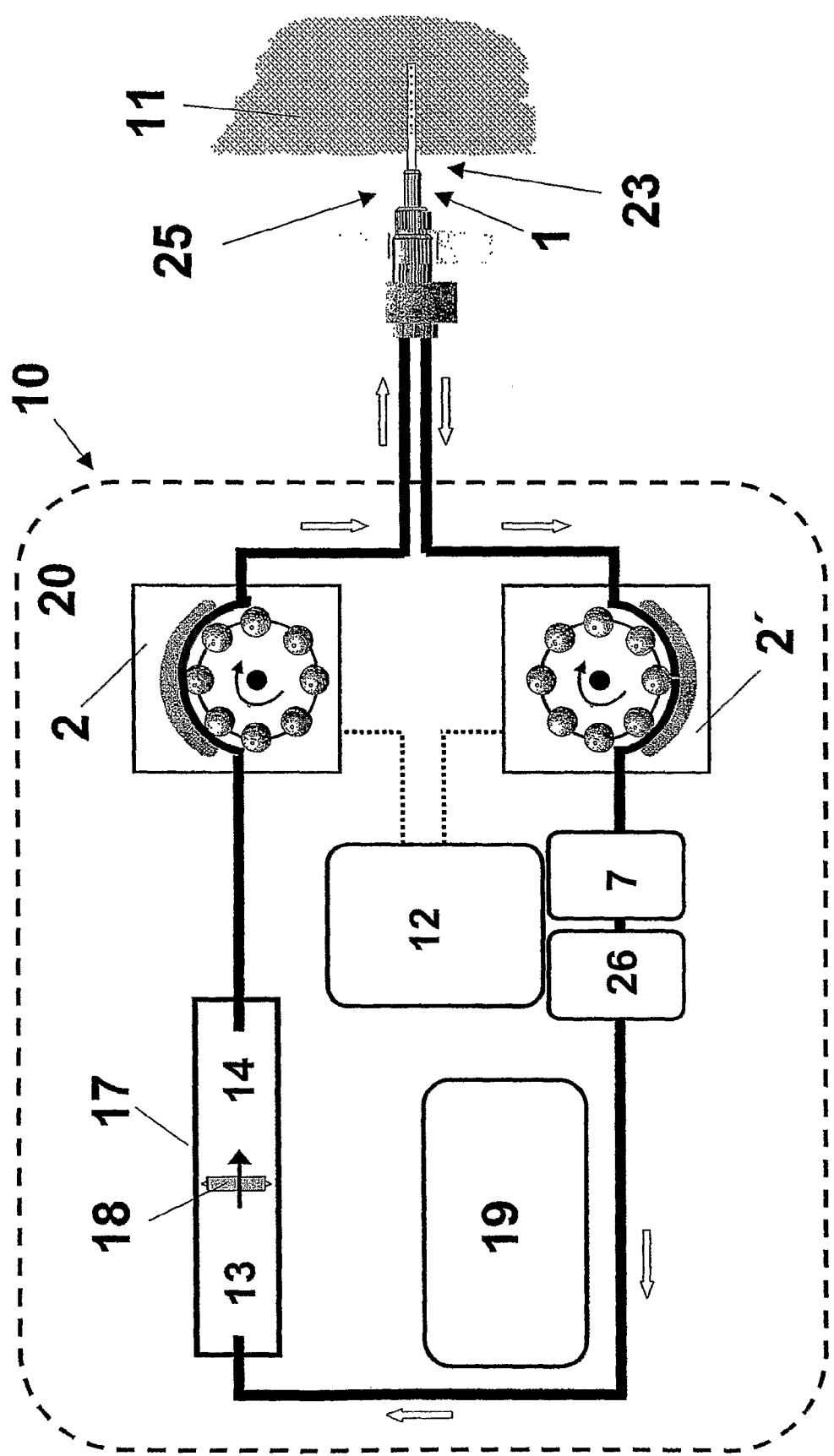

FIG. 7 shows a further embodiment variation, in which two conveyor units 2, 2' for conveying the delivery of the insulin from the container 14 to the catheter 25 and for conveying the perfusion and/or tissue fluid from the catheter 25 to the glucose sensor 7 are provided. The (revolution) speed of the conveyor unit 2 for conveying the insulin is regulated in accordance with the measured tissue glucose concentration. The conveyor unit 2' for conveying the perfusion and/or tissue fluid may also be regulated by the regulatory unit 12. Using this arrangement, a very high efficiency in the insulin delivery may be achieved if the conveyor unit 2 for the insulin is operated at a flow rate (e.g., 7 µl/minute) that is higher than the flow rate of the conveyor unit 2' for conveying the perfusion and/or tissue fluid (e.g., 0.5 µl/minute). The quantity difference between the two fluid flows remains in the subcutaneous tissue 11.

Figure 8:
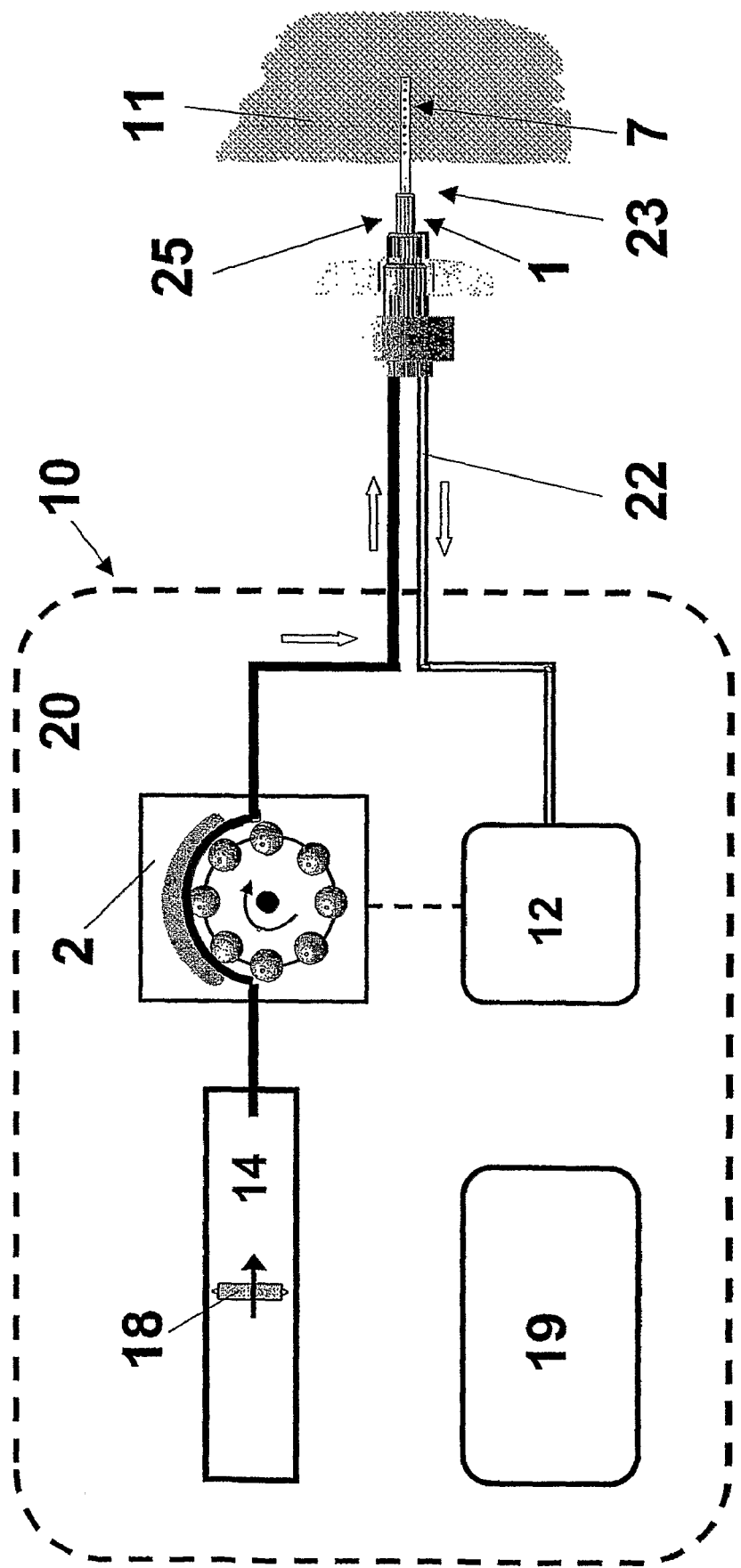

Finally, FIG. 8 shows a further embodiment variation in which, in contrast to the embodiment variation shown in FIG. 6, only one container 14 for insulin is provided and no container 15 for a neutral solution is arranged. This results in a further reduction of the overall size of the unit.

Although not shown in FIG. 6 and FIG. 8, it is possible and advantageous to provide a unit 26 for calibrating the measurement of the tissue glucose concentration in these embodiments. This may allow for a calibration, as described above, for refining the estimation of an appropriate amount of insulin to be administered, for instance based on one or endogenous markers (for instance by measuring the electrical conductivity of the perfusion fluid comprising components of the body fluid, due to diffusion or the like) and/or based on one or more exogenous markers (for instance mannitol provided in the perfusion fluid). Such a calibration unit 26 may also fulfill the function to estimate or detect information with regard to the degree of equilibration (and/or degree of mixture, degree of dilution) of the perfusion fluid with the tissue fluid in the area of influence 24. When a calibration unit 26 is provided in the embodiments of FIG. 6 or FIG. 8, the calibration unit 26 may be located close to the glucose sensor 7.

In a study on seven subjects, it was possible to show that the ratio between blood glucose concentration and glucose concentration in the tissue fluid are strongly correlated even upon the delivery of highly concentrated insulin at the same location as the removal location of the tissue fluid. The local subcutaneous delivery of insulin therefore does not negatively influence the glucose measurement. The glucose may thus be determined reliably via the tissue fluid.

Figure 9:
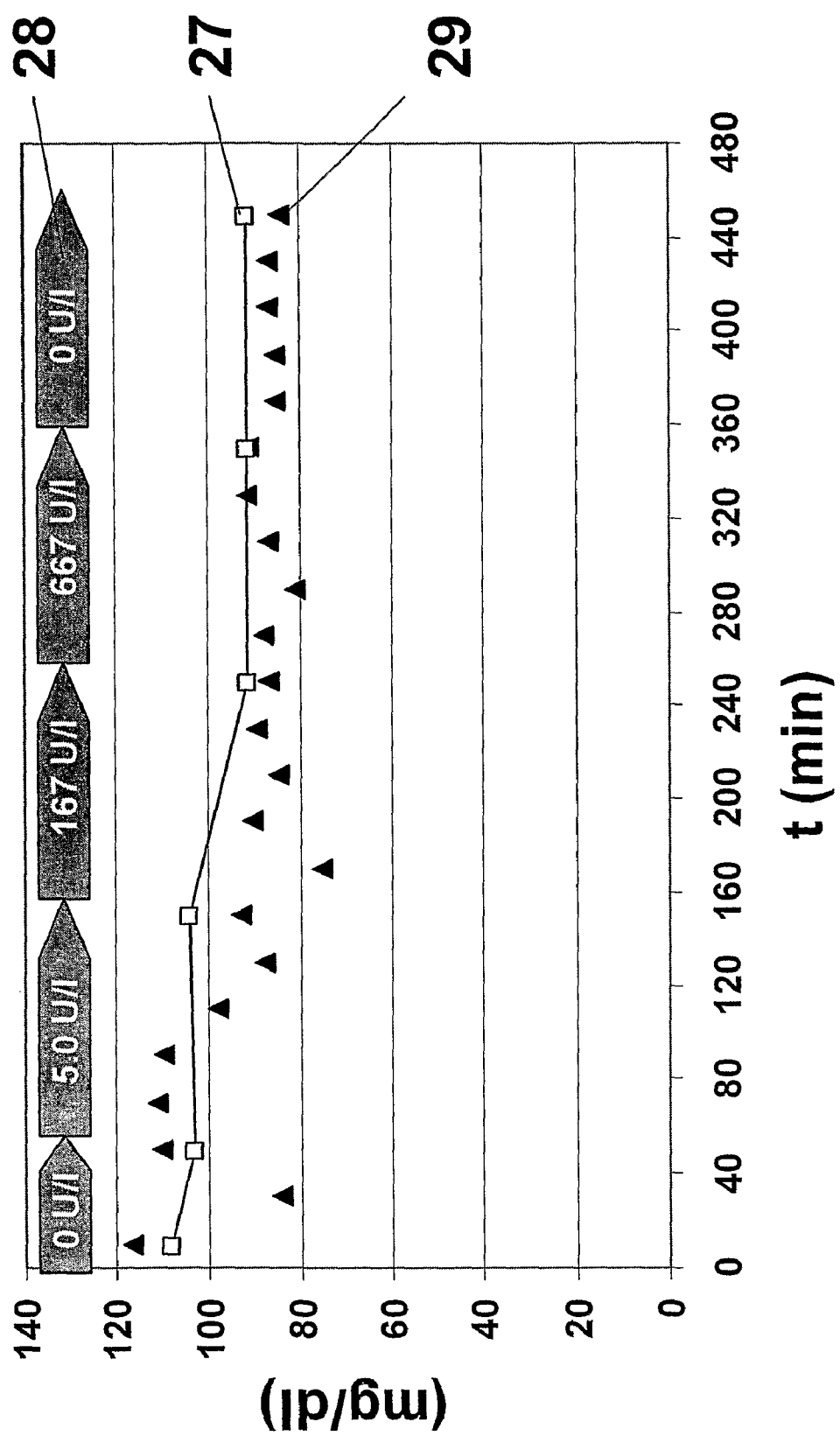
FIG. 9 shows the time curve of the plasma glucose concentration and tissue glucose concentration depending on the time in an experiment on a representative subject.

FIG. 9 shows the representative result of the time curves of the tissue glucose concentration 29, as well as the plasma glucose concentration 27, during an experiment on a healthy subjects, different insulin doses 28 having been delivered using a microdialysis catheter. In these experiments, insulin concentrations of different levels were generated through local insulin infusion at multiple adipose tissue locations with the aid of microperfusion catheters and microdialysis catheters and tissue fluids were simultaneously removed from these locations and the glucose concentration 29 therein was measured. The glucose concentration 27 in the blood was also determined during these experiments for comparison thereto. It was possible to show that even from a relatively low perfusate insulin concentration (at 5 U/l) the ratio between the blood glucose concentration 27 and the glucose concentration 29 in the tissue fluid no longer changed. Even at extremely high insulin concentrations 28, a stable ratio between these two glucose concentrations 29, 27 was observed. These results were surprising, since the cells of the adipose tissue are very sensitive to insulin in regard to glucose uptake.

Figure 10:
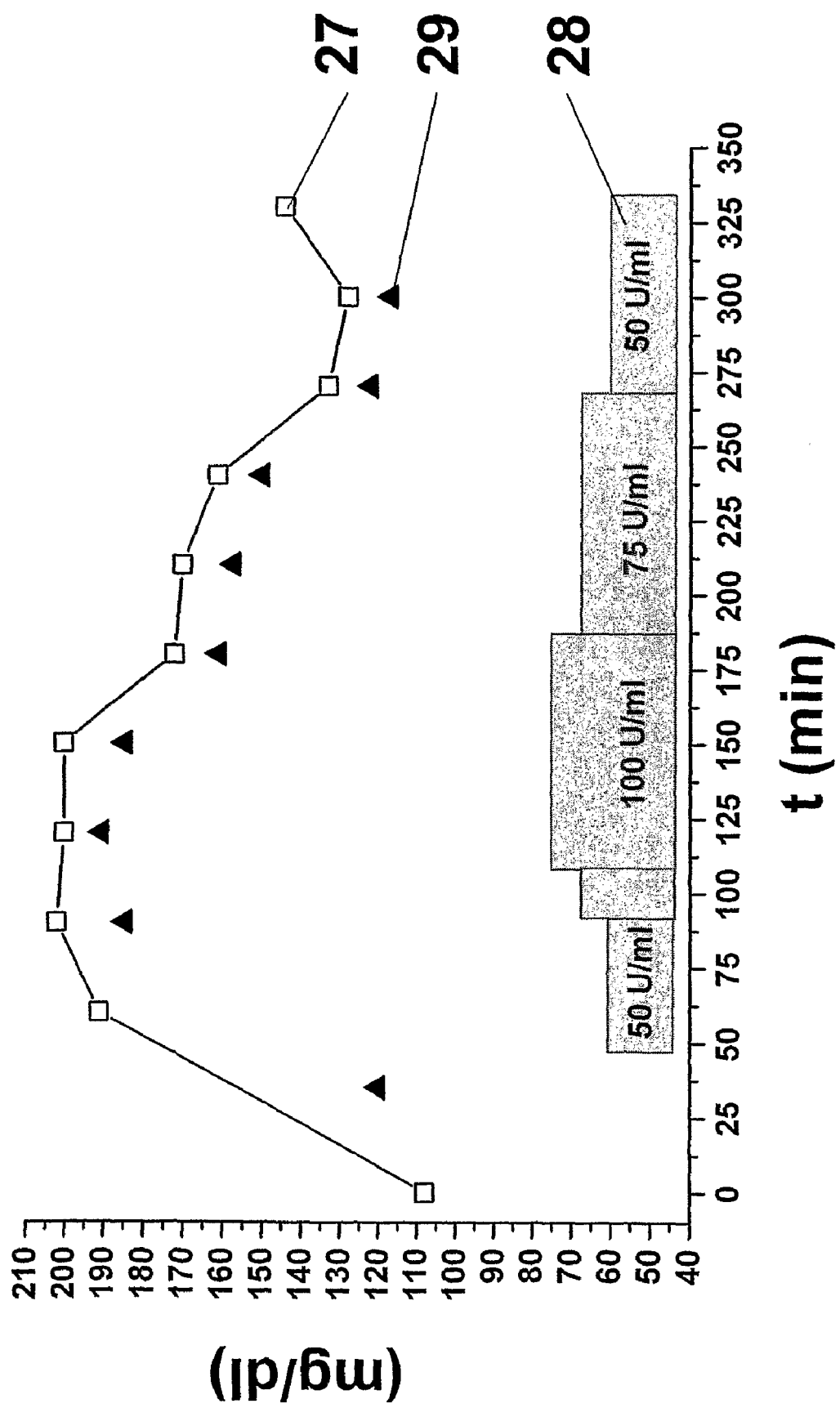
FIG. 10 shows the time curve of the blood glucose and tissue glucose depending on the time in an experiment on a type I diabetic patient.

Finally, FIG. 10 shows a representative measurement result of experiments in a type I diabetic patient who had no residual insulin secretion. The principle of the novel type of insulin supply and simultaneous tissue fluid collection for a continuous glucose measurement was able to be tested successfully. FIG. 10 shows the time curves of the plasma glucose concentration 27, tissue glucose concentration 29, and the delivered insulin concentration 28. Due to the interruption of the typical insulin therapy in the morning, the plasma glucose concentration 27 and the glucose concentration 29 increased in the tissue fluid of this type I diabetic patient. By introducing insulin 28 using a microdialysis catheter, the blood glucose concentration 27 could then again be brought to normoglycemic values. There was a stable ratio between the blood glucose 27 and the glucose 29 in the tissue fluid collected using the same microdialysis catheter during the entire experiment. The close relationship between the tissue glucose concentration 29 and the plasma glucose concentration 27 shows that the measurement of the tissue glucose concentration at the location of the insulin delivery results in a stable ratio between the tissue glucose concentration and the plasma glucose concentration.

Further experiments have shown that the invention is best suitable for the therapy of type I diabetic patients, and that efficient control of the glucose concentration is thus achievable. The device according to the invention may be implemented in an overall size which is comparable to the size of insulin pumps on the market. The reduction in size is possible since the system only has one catheter and therefore typical sender and receiver parts may be dispensed with and the pump and fluidic parts may be implemented singly and not doubly. Since the insulin supply and the collection of tissue fluid is performed at one and the same tissue location using the system, the insulin concentration at this location is strongly elevated, which results in a stable ratio between blood glucose and glucose in the collected tissue fluid. Through these stabilized ratios, improvement of the correlation of the blood glucose concentrations to the glucose values in the tissue fluid may be achieved. By using a catheter for insulin supply and simultaneous tissue fluid collection, the area over which the insulin is exchanged with the tissue fluid is relatively large. An absorption kinetic of the insulin may thus be achieved which is more rapid than in the insulin delivery through typical catheters. This has the positive effect that relatively simple algorithms may be applied for the automated operation of the system. The device according to the invention is especially suitable for continuous glucose measurement and simultaneous, glucose-dependent insulin supply, primarily in type I, but also in type II diabetic patients.

The implementation of the invention is not restricted to the preferred embodiments illustrated in the figures. Rather, multiple variations are conceivable which make use of the achievement of the object illustrated and the principle according to the present invention, even with significantly differently designed embodiments.

Furthermore, it is to be noted that "comprising" does not exclude other elements or steps and "a" or an does not exclude multiples. In addition, it is to be noted that features or steps which have been described with reference to one of the above exemplary embodiment may also be used in combination with other features or steps of other exemplary embodiments described above. Reference numbers in the claims are not to be viewed as limiting.

The invention claimed is:

1. A device for delivery of a physiologically active substance depending on a measured physiological parameter, the device comprising:
    a container for a perfusion fluid containing the physiologically active substance,
    a unit for delivery of the perfusion fluid containing the physiologically active substance into the body,
    a sensor for measuring the physiological parameter of the body by an analysis of the perfusion fluid after an at least partial equilibration of the perfusion fluid with a body fluid,
    a unit, which is connected to the sensor by a signal line, for controlling the quantity of the physiologically active substance to be delivered depending on the measured physiological parameter,
    a unit for calibrating the measurement of the physiological parameter,
    wherein the sensor for measuring the physiological parameter is combined with the unit for delivery of the perfusion fluid containing the physiologically active substance in such a way that a location of the measurement of the body fluid for determining the physiological parameter in the body is in an area of influence of the delivered physiologically active substance, so that the measurement of the physiological parameter occurs essentially at the location of the delivery of the physiologically active substance, and
    wherein the unit for calibrating the measurement of the physiological parameter is formed by a unit for measuring the conductivity of the perfusion fluid after an at least partial equilibration of the perfusion fluid with the body fluid.

2. The device according to claim 1, comprising a unit for removing the perfusion fluid after the at least partial equilibration of the perfusion fluid with the body fluid.

3. The device according to claim 2, wherein, additionally to the sensor, the unit for removing the perfusion fluid after the at least partial equilibration of the perfusion fluid with the body fluid is combined with the unit for delivery of the perfusion fluid containing the physiologically active substance, so that the measurement of the physiological parameter occurs essentially at the location of the delivery of the physiologically active substance.

4. The device according to claim 2, wherein the sensor for measuring the physiological parameter and/or the unit for removing the perfusion fluid after the at least partial equilibration of the perfusion fluid with the body fluid is combined with the unit for delivery of the perfusion fluid containing the physiologically active substance, so that the measurement of the physiological parameter occurs essentially in the perfusion fluid after at least partial equilibration with the body fluid.

5. The device according to claim 1, wherein the unit for delivery of the perfusion fluid containing the physiologically active substance is adapted for its delivery in at least one of the group consisting of subcutaneous tissue, cutaneous tissue, an organ, a vein, an artery, and a blood vessel.

6. The device according to claim 1, wherein the unit for controlling the quantity of the physiologically active substance to be delivered depending on the measured physiological parameter is adapted to regulate the quantity of the physiologically active substance to be delivered depending on the measured physiological parameter.

7. The device according to claim 2, wherein the unit for removing the perfusion fluid after the at least partial equilibration of the perfusion fluid with the body fluid comprises at least one of the group consisting of a microdialysis unit, a microperfusion unit, an ultrafiltration unit, a suction unit using a microneedle, and a transdermal extraction unit using reverse iontophoresis, ultrasound and/or osmotic pressure.

8. The device according to claim 2, wherein the unit for removing the perfusion fluid after the at least partial equilibration of the perfusion fluid with the body fluid and the unit for delivery of the physiologically active substance are formed by a shared catheter for removing the fluid and/or measuring the physiological parameter and/or delivering the physiologically active substance.

9. The device according to claim 8, wherein the catheter is formed by one of the group consisting of a microdialysis catheter, a microperfusion catheter, an ultrafiltration catheter, and an iontophoresis/reverse iontophoresis catheter.

10. The device according to claim 8, wherein the catheter is formed by a double-lumen catheter, a perfusion fluid or a mixture of a perfusion fluid and the fluid removed from the body being suctioned through one lumen and the physiologically active substance being delivered via the other lumen.

11. The device according to claim 2, wherein the sensor is integrated in the unit for removing the perfusion fluid after the at least partial equilibration of the perfusion fluid with the body fluid and/or in the unit for delivery of the physiologically active substance.

12. The device according to claim 1, wherein a unit for conveying the perfusion fluid containing the physiologically active substance from the container for the perfusion fluid containing the physiologically active substance to the unit for delivery of the physiologically active substance is provided.

13. The device according to claim 2, wherein a unit for conveying a perfusion fluid and/or the fluid removed from the body from the unit for removing the perfusion fluid after the at least partial equilibration of the perfusion fluid with the body fluid to the sensor is provided.

14. The device according to claim 7, wherein the unit for conveying the perfusion fluid containing the physiologically active substance is simultaneously usable for conveying the perfusion fluid and/or the fluid removed from the body from the unit for removing the perfusion fluid after the at least partial equilibration of the perfusion fluid with the body fluid to the sensor.

15. The device according to claim 1, wherein multiple containers for perfusion fluid containing physiologically active substance, preferably of different concentrations of the physiologically active substance, are provided.

16. The device according to claim 1, wherein a container for a neutral solution is provided.

17. The device according to claim 16, wherein the at least one container for the perfusion fluid containing the physiologically active substance and the container for the neutral solution are connected to a changeover switch, which is connected to the unit for controlling the quantity of the physiologically active substance to be delivered depending on the measured physiological parameter, so that the quantity of the physiologically active substance delivered is adjustable by actuating the changeover switch.

18. The device according to claim 17, wherein the at least one container for the perfusion fluid containing the physiologically active substance and the container for the neutral solution are connected to a mixer, which is connected to the unit for controlling the quantity of the physiologically active substance to be delivered depending on the measured physiological parameter, so that the delivered quantity of the physiologically active substance is adjustable by actuating the mixer.

19. The device according to claim 1, wherein at least one container for collecting analyzed perfusion fluid and/or fluid removed from the body is provided.

20. The device according to claim 19, wherein the collecting container and the at least one container for the perfusion fluid containing the physiologically active substance and/or the container for the neutral solution are each formed by a shared container having a movable wall for separating the perfusion fluid containing the physiologically active substance and/or the neutral solution from the collected perfusion fluid and/or the fluid removed from the body.

21. The device according to claim 1, wherein the at least one container for the perfusion fluid containing the physiologically active substance, and optionally the container for the neutral solution, is or are implemented as refillable.

22. The device according to claim 1, wherein the unit for calibrating the measurement of the physiological parameter is adapted to determine a degree of equilibration of the perfusion fluid with the body fluid.

23. The device according to claim 1, wherein the at least one container for the perfusion fluid containing the physiologically active substance, a container for a neutral solution, a container for collecting analyzed fluid removed from the body, the unit for delivery of the perfusion fluid containing the physiologically active substance, the unit for controlling the quantity of the physiologically active substance to be delivered, and the calibration unit are positioned in a shared housing.

24. A method for the delivery of a physiologically active substance depending on a measured physiological parameter, the method comprising:
   delivering a perfusion fluid containing the physiologically active substance into a body,
   measuring the physiological parameter of the body in such a way that a location of measurement of the body fluid for determining the physiological parameter in the body is in an area of influence of the delivered physiologically active substance by an analysis of the perfusion fluid after an at least partial equilibration of the perfusion fluid with a body fluid, and
   controlling the quantity of the physiologically active substance delivered depending on the measured physiological parameter by way of a sensor and a signal line,
   wherein the physiological parameter is measured essentially at the location at which the physiologically active substance is delivered.

25. The method according to claim 24, comprising removing the perfusion fluid from the body after the at least partial equilibration of the perfusion fluid with the body fluid.

26. The method according to claim 24, wherein the physiological parameter is measured essentially in the perfusion fluid after an at least partial equilibration with the body fluid.

27. The method according to claim 24, wherein the physiologically active substance is mixed with a neutral solution before the delivery.

28. The method according to claim 24, wherein the physiologically active substance is mixed with a neutral solution in subcutaneous tissue.

29. The method according to claim 24, wherein the physiologically active substance is mixed with a neutral solution in predefined ratios and provided for delivery in the predefined mixing ratios.

30. The method according to claim 24, wherein the measurement of the physiological parameter is calibrated, preferably permanently.

* * * * *